United States Patent [19]

Druliner

[11] Patent Number: 5,440,067
[45] Date of Patent: Aug. 8, 1995

[54] CATALYZED GAS PHASE ISOMERIZATION OF NONCONJUGATED 2-ALKYL-3-MONOALKENENITRILES

[75] Inventor: Joe D. Druliner, Newark, Del.

[73] Assignee: E. I. DuPont de Nemours and Company, Wilmington, Del.

[21] Appl. No.: 341,726

[22] Filed: Nov. 18, 1994

[51] Int. Cl.$^6$ ............................................. C07C 253/30
[52] U.S. Cl. ................................................. 558/355
[58] Field of Search ......................................... 558/355

[56] References Cited

U.S. PATENT DOCUMENTS

| | | | |
|---|---|---|---|
| 3,676,481 | 7/1972 | Chia | 558/355 |
| 3,739,011 | 6/1973 | Drinkard, Jr. | 558/355 |
| 3,766,237 | 10/1973 | Chia et al. | 260/465.3 |
| 3,852,325 | 12/1974 | King | 558/355 |
| 3,852,328 | 12/1974 | Chia et al. | 558/355 |
| 3,852,329 | 12/1974 | Tomlinson | 558/355 |
| 3,853,948 | 12/1974 | Drinkard, Jr. et al. | 558/355 |
| 4,298,546 | 11/1981 | McGill | 558/355 |
| 4,783,546 | 11/1988 | Burke et al. | 558/355 |

OTHER PUBLICATIONS

Kurokawa, H. et al., "Skeletal Rearrangement of Unsaturated Nitriles over Solid-Base catalysts", *Journal of Catalysis*, 141, pp. 94–101 (1993).

*Primary Examiner*—Joseph Paul Brust

[57] ABSTRACT

A gas phase process for the catalytic isomerization of 2-alkyl-3-monoalkenenitriles to 3- and/or 4-monoalkene nitriles, wherein a supported composition of zero-valent nickel and bidentate phosphite ligand is used as the catalyst.

12 Claims, No Drawings

CATALYZED GAS PHASE ISOMERIZATION OF NONCONJUGATED 2-ALKYL-3-MONOALKENENITRILES

FIELD OF THE INVENTION

This invention generally relates to a gas phase process for the isomerization of 2-alkyl-3-monoalkenenitriles to produce 3- and/or 4-monoalkene linear nitriles. In particular, the invention relates to a gas phase process for the isomerization of 2-alkyl-3-monoalkeneitriles to produce 3 and/or 4-monoalkene linear nitriles by using zero-valent nickel and a bidentate phosphite ligand.

BACKGROUND OF THE INVENTION

Hydrocyanation of butadiene to form pentenenitrile (PN) is known in the art, e.g., U.S. Pat. No. 3,766,237. The predominant pentenenitriles so formed, e.g., 3-pentenenitrile, 4-pentenenitrile and 2-methyl-3-butenenitrile, are further subjected to hydrocyanation and/or isomerization to form adiponitrile (ADN), a commercially important material in the synthesis of nylon.

In the liquid phase, 2-methyl-3-butenenitrile can be efficiently isomerized to 3- and/or 4-pentenenitrile, in the presence of zero-valent nickel catalysts, which products are easily further hydrocyanated to form adiponitrile. No such techniques for carrying out this isomerization in the gas phase are known. A related study by Kurokawa et al., (Journal of Catalysis, 141, 94–101 (1993)) describes the gas phase isomerization of 3-pentenenitrile to a mixture of branched and linear pentenenitriles. Catalysts used include $SiO_2$, MgO or CaO, at temperatures of 350° C. and 370° C. Ratios of branched to linear products in the range of 19/35, 24/18 and 10/49 were reported. In all cases, only conjugated branched compounds were obtained; that is, no 2-methyl-3-butenenitrile was formed.

SUMMARY OF THE INVENTION

The present invention provides a process for the gas phase isomerization of an acylic, aliphatic, nonconjugated 2-alkyl-3-monoalkenenitrile, preferably 2-methyl-3-butenenitrile, said process comprising contacting the starting nitrile, at a temperature within the range of about 135° C. to about 170° C., with a supported catalyst composition comprising zero-valent nickel and at least one bidentate phosphite ligand selected from the group consisting of Formula I and II:

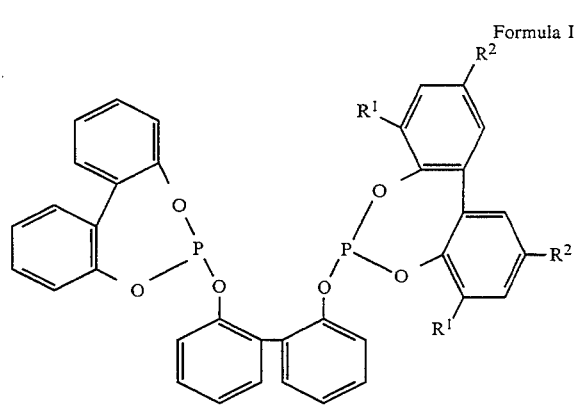

Formula I wherein each $R^1$, independently, is a secondary or tertiary hydrocarbyl of 3 to 12 carbon atoms;

each $R^2$, independently, is H, a $C_1$ to $C_{12}$ alkyl, or $OR^3$, wherein $R^3$ is $C_1$ to $C_{12}$ alkyl; and

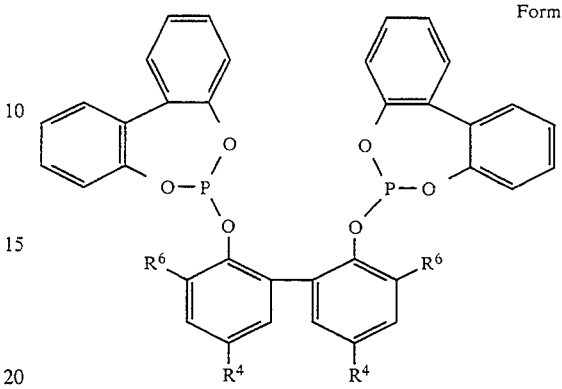

Formula II wherein each $R^4$, independently, is a tertiary hydrocarbon of up to 12 carbon atoms, or $OR^5$, wherein $R^5$ is a $C_1$ up to $C_{12}$ alkyl; and each $R^6$, independently, is a tertiary hydrocarbon of up to 12 carbon atoms, to produce nonconjugated, linear, acyclic 3- and 4-monoalkene nitriles, preferably 3- and 4-pentenenitriles.

In the above definitions for both Formula I and Formula II, "secondary" and "tertiary" refer to the carbon atom attached to the aromatic ring. In addition, for purposes of the present disclosure and claims, the terms "alkenenitrile", "pentenenitrile", and "butenenitrile" are intended to mean, respectively, a cyanoalkene in which the carbon atom of the cyano group is the first carbon; a cyanobutene; and a cyanopropene.

The present invention provides a catalyzed gas phase process which is rapid, selective, efficient and stable in the isomerization of nonconjugated 2-alkyl-3-monoalkenenitriles. Advantages of this gas phase process include the elimination of certain solvents used in most liquid phase processes, such as reaction diluents or product extractants. Furthermore, in the gas phase process, the catalyst is utilized as a stationary solid phase, which can reduce catalyst synthesis, recovery, recycle and by-product waste disposal costs. Such advantages can eliminate the need for equipment associated with liquid phase processes and provide further cost savings.

DETAILED DESCRIPTION OF THE PREFERRED EMBODIMENTS

When the starting nitrile is 2-methyl-3-butenenitrile (2M3BN), the gas phase isomerization process of this invention produces a mixture of pentenenitriles consisting essentially of 3-pentenenitrile (3PN) and 4-pentenenitrile (4PN).

Zero-valent nickel is known in the art and can be made in a number of ways. Most common zero-valent nickel species, which can be used to form catalytic compositions useful in the present invention, are derived from Ni(O) complexes containing o-tritolylphosphite, p-tritolylphosphite, cyclooctadiene, and ethylene. Ni(O) can also be prepared by reduction of Ni(II) compounds with molecular hydrogen, or other reducing agents, in the presence of appropriate ligands (e.g., see Example 2 hereinafter where $Ni(NO_3)_2$ is reduced by $H_2$ to provide Ni(O) on silica gel. Moreover, Ni(O)

complexes containing bidentate ligands can be prepared from reduction of Ni(II) compounds (e.g., see Example 1 hereinafter where Ni(ligand A)(ethylene) is prepared) and Ni metal and a bidentate ligand. Other zero-valent nickel species known to those skilled in the art can be successfully used as well.

The actual catalyst is a complex of zero-valent nickel with the bidentate phosphite ligand, which is formed when those two materials are combined. An effective catalyst requires at least one mole of bidentate phosphite ligand for one gram-atom of zero-valent nickel.

The above catalyst compositions normally are supported on a carrier of silica, alumina, carbon, or other suitable support. Unsupported catalysts may work in some cases but their catalytic efficiency might be low. Commonly used techniques for treatment of supports with metal catalysts can be found in B. C. Gates, *Heterogeneous Catalysis*, Vol. 2, pp. 1–29, Ed. B. L. Shapiro, Texas A & M University Press, College Station, Texas, 1984. Alternately, a given support can be prepared with a uniformly dispersed coating of zero-valent nickel metal, and then can be treated with the desired bidentate phosphite ligand.

Typically, in accordance with this invention, the zero-valent nickel catalysts are dispersed on silica, alumina or carbon supports at concentrations sufficient to produce a supported catalyst composition containing 0.3 wt. % to 1.0 wt. % Ni. The catalyst compositions are then loaded into tubular reactors, and gaseous 2-alkyl-3-monoalkenenitrile, e.g., 2-methyl-3-butenenitrile, is passed continuously over the solid catalysts at temperatures sufficiently high to maintain both the starting nitrile and the isomerization products in the gas phase.

The preferred temperature range is from about 140° C. to about 160° C., most preferably from about 145° C. to about 150° C. The temperature must be high enough to keep all the organic materials volatilized, but low enough to prevent deterioration of the catalyst. The preferred temperature is dependent to a certain extent on the particular catalyst employed, the particular 2-alkyl-3-monoalkenenitrile being used, and the desired reaction rate. Operating pressure is not particularly critical and can conveniently be from about 1 to about 10 atmospheres (101.3 to 1013 kPa). No economic benefit can be expected above that range.

The 2-alkyl-3-monoalkenenitrile starting material can be delivered either as a neat vapor or as a vaporized solution in a solvent, such as acetonitrile or toluene. Under atmospheric pressure, using an additional feed of nitrogen or another inert gas as a carrier, temperatures of 140°–150° C. are typically used. Nitrogen is preferred because of its low cost. Gaseous oxygen, water vapor, or other gaseous substance which could react with either the catalyst or the starting 2-alkyl-3-monoalkenenitrile should be avoided. The isomerization products are liquid at room temperature and can be conveniently recovered by cooling.

The olefinic double bond in the 2-alkyl-3-monoalkenenitriles used as the starting materials in the process of this invention cannot be conjugated to the triple bond of the cyano group. Suitable starting 2-alkyl-3-monoalkenenitriles can also carry groups which do not attack the catalyst, for example another cyano group. Preferably, the starting 2-alkyl-3-monoalkenenitriles contain from 5 to 8 carbon atoms, excluding any additional substitution. 2-methyl-3-butenenitrile is especially important in the production of adiponitrile. Other representative nitriles include 2-ethyl-3-butenenitrile and 2-propyl-3-butenenitrile.

The following Formulas III and IV illustrate suitable representative starting 2-alkyl-3-monoalkeneitriles. When the starting nitrile is 2-methyl-3-butenenitrile, the isomerization products are those shown in Formulas V and VI.

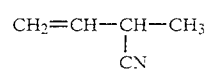  Formula III

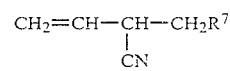  Formula IV wherein
$R^7$ is H or a $C_1$ to $C_3$ alkyl.

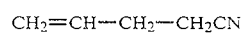  Formula V and

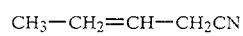  Formula VI

It will be recognized that Formula III is a special case of Formula IV, where $R^7$ is hydrogen.

The present isomerization process can be carried out, for example, by first charging a tubular reactor with a particular supported catalyst composition, preferably in an inert atmosphere, and then connecting it to a continuous feeding and recovery system while minimizing air contact by suitably purging all feed lines with a flow of an inert gas, such as nitrogen, argon, or helium. The reactor, equipped with a thermocouple, is then heated to the desired reaction temperature, either under a continuous flow of inert gas, or with both the inlet and the outlet closed, while the inert gas is flowing through a bypass. The starting 2-alkyl-3-monoalkenenitrile can be fed either neat or dissolved in a suitable solvent, such as, for example, acetonitrile or toluene. The starting nitrile and any solvent are passed through a portion of the feed line heated to the reaction temperature to ensure complete vaporization. The gaseous product mixture exiting through the reactor outlet can be passed, if desired, through a heated gas sampling loop of a gas chromatograph for monitoring the progress of the reaction. Alternatively, the gaseous effluent can be cooled to 0°–25° C. in order to recover the products as liquids. The mole ratio of unsaturated compound to catalyst, per hour of continuous feed, normally can be varied from about 5:1/hour to 100:1/hour.

The isomerization reaction is preferably carried out without a solvent. If any solvent is used, it should be gaseous at the reaction temperature and pressure and inert towards the starting nitrile, the reaction products, and the catalyst. Typical solvents include hydrocarbons such as hexane, benzene, toluene, and xylene, or nitriles such as acetonitrile.

EXAMPLES

The following non-limiting, representative examples illustrate the present invention. All proportions and percentages are by weight unless otherwise indicated. In the examples, Ligand "A" is the ligand of Formula II, where each $R^4$ is $OCH_3$, and each $R^6$ is t-butyl.

EXAMPLE 1

Synthesis of a carbon supported Ni(0) (Ligand "A")$CH_2$=$CH_2$, where the Ligand "A" is of Formula II, where each $R^4$ is $OCH_3$ and each $R^6$ is t-butyl All operations were carried out in a nitrogen-filled glove box. Into a glass vial were placed 0.385 g (1.5 mmoles) Ni(acetylacetonate)$_2$, 1.18 g (1.5 mmoles) Ligand "A", and 20 ml toluene. Next, ethylene was bubbled through the solution. Thereafter, 2.3 ml of a 1.9M toluene solution of $(C_2H_5)_3$Al (4.4 mmoles) was added dropwise while ethylene continued to be bubbled through the solution. After several more minutes, the ethylene flow was discontinued, and the vial was sealed with a septum. The reaction contents were stirred overnight. The next day, about half of the solvent was removed at a reduced pressure. A portion of the solid reaction product was recovered by filtration. Methanol was added to the filtrate to precipitate additional solid reaction product. Recovered product was dried under vacuum to yield 0.78 g of a gold-colored powder. A $^{31}$P NMR spectrum of the final product exhibited a major singlet at 169.9 ppm {Ni(Ligand "A")$CH_2$=$CH_2$) and a minor singlet at 162.8 ppm {(Ni(Ligand "A")$_2$}.

A 5 g sample of acid-washed carbon was placed in a quartz tube and heated in a tube furnace under a stream of nitrogen to 100° C. for 1 hour. The tube was cooled to room temperature, sealed, and transferred to a nitrogen-filled glove box. The dried carbon was then stirred for 30 minutes with a solution of 0.5 g (0.57 mmole) of {Ni{Ligand "A")$CH_2$=$CH_2$} in 10 ml of dry toluene. Toluene solvent was evaporated under vacuum to afford a dry {Ni{Ligand "A")$CH_2$=$CH_2$}/C catalyst.

EXAMPLE 2

Synthesis of a $SiO_2$ supported Ni(0) (Ligand "A")$_2$ where the Ligand "A" is of Formula II where each $R^4$ is $OCH_3$, and each $R^6$ is t-butyl In a glass reactor there were placed 0.25 g (0.86 mmole) of Ni(NO$_3$)$_2$.6 H$_2$O and 25 ml of water. To the resulting solution there was added 10 g of silica granules. The mixture was stirred, then dried under vacuum. The resulting Ni(NO$_3$)$_2$-coated silica was further dried by heating under a stream of nitrogen in a quartz tube. The temperature was gradually raised from room temperature to 300° C. at a rate of 30° C./minute and held at 300° C. for 1 hour. The flow of nitrogen was discontinued, and a flow of hydrogen was started. The temperature was raised to 500° C. in one hour and held for 2 hours. The tube contents were cooled to room temperature, then transferred to a nitrogen-filled glove box.

In a 20 mL glass vial, 1.28 g of the resulting $SiO_2$-supported zero-valent nickel was treated with 0.17 g (0.22 mmole) of Ligand "A" dissolved in 5 mL of dry toluene. The mixture was stirred for 10 minutes; then toluene was removed under vacuum, to yield solid {Ni(0)+(Ligand "A")$_2$/$SiO_2$} catalyst.

EXAMPLES 3-11

Gas Phase Isomerization of 2-methyl-3-butenenitrile

In a nitrogen-filled glove box, a plug of glass wool was placed in the bottom of an empty 0.25-inch (0.64 cm) diameter x 15-inch (38.1 cm) long stainless steel tubular reactor. Then, the amount and type of Ni(0) catalyst shown in Table 1 was introduced into the reactor. In all the examples using a catalyst composition comprising a bidentate phosphite ligand, the ligand was Ligand "A". The reactor was then connected to a feed and product recovery system purged with nitrogen. The starting nitrile was fed either as a 8.2–10.6% solution of 2M3BN in acetonitrile or as neat 2M3BN. Attached to the exit side of the reactor was a jacketed receiver with circulating ethylene glycol cooled to 0° C. The liquid products were periodically removed and analyzed by gas chromatography (GC). GC analyses were done on a 30 m DB-23 capillary column of a 0.32 mm internal diameter, supplied by J & W Scientific, Folsom, Calif. A 0.5% solution of 1-cyanooctane in toluene, which served as an internal GC standard, also was fed to the receiver. The nitrogen, 2M3BN, and acetonitrile feed streams were preheated to 165° C. to ensure complete vaporization. The reactor was heated in a split tube furnace to the temperature shown in Table 1. Product samples were collected, approximately every hour.

Table 1 summarizes the experimental conditions as well as the results. By "% conv." is meant $$100 \times \frac{\text{(measured GC area \% for 3PN + 4PN)}}{\text{(measured GC area \% for 3PN + 4PN + 2M3BN)}}$$

The starting 2M3BN, used as feed, contained small amounts of 3 PN and 4PN, corresponding to about a 1.5% conversion, which is included in the data reported below. Examples 5, 6, and 7, using the same catalyst, show that silica is a more preferable support than either carbon or alumina. Experiments in Examples 8 and 11, which both used a zero-valent nickel species as a catalyst, in the absence of a bidentate phosphite ligand, gave only very low conversions. In the Table, "A" stands for Ligand "A"; "PTTP" stands for p-tritolyl phosphite; "OTPP" stands for o-tritolyl phosphite.

TABLE 1

| | | | | | | | | | |
|---|---|---|---|---|---|---|---|---|---|
| | | | Gas Phase Isomerization of 2M3BN to 3PN and 4PN | | | | | | |
| Ex. | Catalyst (Support) | Catalyst g, % Ni | 2M3BN Feed Mmole/hr | N2 Feed mL/min | 2M3BN/Ni mole/gramatom | Temp. °C. | Elapsed Time hr. | (3PN) (4PN) GC Area % | % Conv. |
| 3 | Ni["A"]$CH_2$=$CH_2$ (Carbon) | 0.61, 0.61 | 1.0 | 5 | 15.7 | 150 | 1 | 0.98  0.01 | 76 |
| | | | | | | 150 | 2 | 1.64  0.03 | 69 |
| | | | | | | 150 | 3 | 1.48  0.02 | 53 |
| | | | | | | 150 | 4 | 1.10  0 | 38 |
| | | | | | | 150 | 5 | 0.87  0 | 30 |
| 4 | Ni["A"]$CH_2$=$CH_2$ ($SiO_2$) | 1.12, 0.47 | 0.95 | 10 | 10.6 | 145 | 1 | 2.18  0.14 | 89.6 |
| | | | | | | 145 | 2 | 2.89  0.13 | 92.1 |
| | | | | | | 145 | 3 | 3.05  0.11 | 91.9 |
| | | | | | | 145 | 4 | 3.14  0.10 | 91.8 |
| | | | | | | 145 | 5 | 3.08  0.09 | 91.6 |
| | | | | | | 145 | 6 | 3.09  0.08 | 91.4 |
| 5 | Ni["A"]$_2$ | 1.0, 0.35 | 1 | 10 | 16.7 | 145 | 1 | 0.08  0 | 1.5 |
| | Catalyst pre-treated with 2 eq. of $(C_2H_5)_3$ Al/eq. Ni | | | | | 145 | 2 | 0.10  0 | 1.9 |

TABLE 1-continued

Gas Phase Isomerization of 2M3BN to 3PN and 4PN

| Ex. | Catalyst (Support) | Catalyst g, % Ni | 2M3BN Feed Mmole/hr | N2Feed mL/min | 2M3BN/Ni mole/gramatom | Temp. °C. | Elapsed Time hr. | (3PN) GC Area % | (4PN) GC Area % | % Conv. |
|---|---|---|---|---|---|---|---|---|---|---|
|  | (Al2O3) |  |  |  |  | 145 | 3 | 0.10 | 0 | 2.0 |
| 6 | Ni["A"]2 (SiO2) | 1.0, 0.33 | 1 | 10 | 17.8 | 145 | 1 | 2.84 | 0.26 | 88.8 |
|  |  |  |  |  |  | 145 | 2 | 3.37 | 0.30 | 91.8 |
|  |  |  |  |  |  | 145 | 3 | 3.47 | 0.28 | 92.4 |
|  |  |  |  |  |  | 145 | 4 | 3.56 | 0.24 | 91.8 |
|  |  |  |  |  |  | 145 | 5 | 3.57 | 0.20 | 90.8 |
|  |  |  |  |  |  | 145 | 5.5 | 3.54 | 0.18 | 90.3 |
| 7 | Ni["A"]2 (Carbon) | 1.05, 0.35 | 5.1 | 10 | 81.3 | 150 | 1 | 0.01 | 0 | 0.9 |
|  |  |  |  |  |  | 150 | 2 | 0.26 | 0 | 5.0 |
|  |  |  |  |  |  | 150 | 3 | 0.34 | 0 | 6.1 |
|  |  |  |  |  |  | 150 | 4 | 0.31 | 0 | 5.5 |
| 8 | Ni[PTTP]4 (Carbon) | 1.00, 1.14 | 1 | 10 | 5.1 | 145 | 1 | 0.05 | 0 | 10.6 |
|  |  |  |  |  |  | 145 | 2 | 0.07 | 0 | 7.1 |
|  |  |  |  |  |  | 145 | 3 | 0.07 | 0 | 4.1 |
|  |  |  |  |  |  | 145 | 4 | 0.08 | 0 | 3.0 |
| 9 | Ni + 2["A"] (SiO2) | 1.63, 0.47 | 0.95 | 10 | 7.3 | 145 | 1 | 0.42 | 0 | 10.1 |
|  |  |  |  |  |  | 145 | 2 | 0.55 | 0 | 13.8 |
|  |  |  |  |  |  | 145 | 3 | 0.55 | 0 | 13.8 |
|  |  |  |  |  |  | 145 | 4 | 0.51 | 0 | 12.9 |
|  |  |  |  |  |  | 145 | 5 | 0.47 | 0 | 11.7 |
| 10 | Ni[OTTP]2CH2=CH2 (+ "A") (Carbon) | 1.00, 0.42 | 0.95 | 10 | 13.3 | 145 | 1 | 0.19 | 0 | 25.3 |
|  |  |  |  |  |  | 145 | 2 | 0.70 | 0.03 | 23.8 |
|  |  |  |  |  |  | 145 | 3 | 0.72 | 0 | 19.5 |
|  |  |  |  |  |  | 145 | 4 | 0.63 | 0 | 16.4 |
|  |  |  |  |  |  | 145 | 5 | 0.57 | 0 | 14.6 |
| 11 | Ni[OTTP]2CH2=CH2 (Carbon) | 1.04, 0.37 | 5.1 | 10 | 77.7 | 150 | 1 | 0.07 | 0 | 1.3 |
|  |  |  |  |  |  | 150 | 2 | 0.08 | 0 | 1.5 |
|  |  |  |  |  |  | 150 | 3 | 0.10 | 0 | 1.5 |
|  |  |  |  |  |  | 150 | 4 | 0.09 | 0 | 1.6 |
|  |  |  |  |  |  | 150 | 5 | 0.08 | 0 | 1.5 |

EXAMPLES 12-13

Gas Phase Isomerization of 2-methyl-3-butenenitrile Monitored By On-Line GC Analysis The same reactor and procedures as described for Examples 3-11 were used but were adapted to the needs of the continuous, GC-monitored process. The feed and outlet lines were purged with reaction gases. The outlet line was connected to a gas chromatograph, both the line and the sampling valve being heated to 165° C. The reaction temperature was 145° C.; the catalyst in Example 12 was Ni(Ligand "A")2/SiO2 and in Example 13 {Ni{OTTP}2CH2=CH2+Ligand "A"}/SiO2. The starting 2M3BN feed contained both 3PN and 4PN, together corresponding to about a 10.9% conversion, which is included in the results reported below. Total percentage amount of PN was determined as $$100 \times \frac{(GC \text{ area } \% \text{ of all pentenenitrile peaks})}{(GC \text{ area } \% \text{ of all } GC \text{ peaks } - \text{ trace } BD \text{ and } HCN \text{ peaks})}$$

Percent amount of useful PN was determined as $$100 \times \frac{(GC \text{ area } \% \text{ of } 3PN + 4PN + 2M3BN)}{(GC \text{ area } \% \text{ of total } PN)}$$

The experimental conditions as well as the results are given for Example 12 in Table 2 and for Example 13 in Table 3, below.

TABLE 2

Gas Phase Isomerization of 2M3BN to 3PN and 4PN at 145° C.

| Ex. | Catalyst (Support) | Catalyst g, wt. % Ni | 2M3BN Feed mmole/hr | N2 Feed mL/min | 2M3BN/Ni mole/gramatom | Elapsed Time Hr. | % Conv. | % PN/ Total | (3PN) GC Area % | (4PN) GC Area % | % Useful PN |
|---|---|---|---|---|---|---|---|---|---|---|---|
| 12 | Ni["A"]2 (SiO2) | 0.99, 0.33 | 2.06 | 10 | 26.9 | 1 | 92.3 | 89.7 | 32.62 | 2.77 | 45.5 |
|  |  |  |  |  |  | 2 | 92.8 | 97.7 | 62.66 | 5.51 | 78.4 |
|  |  |  |  |  |  | 3 | 92.6 | 98.1 | 62.49 | 4.76 | 77.2 |
|  |  |  |  |  |  | 4 | 92.5 | 98.6 | 65.28 | 3.72 | 77.8 |
|  |  |  |  |  |  | 5 | 92.4 | 99.0 | 67.00 | 3.10 | 78.5 |
|  |  |  |  |  |  | 6 | 92.1 | 98.5 | 67.04 | 2.81 | 78.3 |
|  |  |  |  |  |  | 7 | 92.4 | 98.6 | 67.58 | 2.60 | 78.3 |
|  |  |  |  |  |  | 8 | 92.0 | 98.9 | 67.99 | 2.23 | 78.2 |
|  |  |  |  |  |  | 9 | 92.5 | 99.0 | 69.31 | 2.08 | 79.0 |
|  |  |  |  |  |  | 10 | 91.7 | 98.9 | 68.29 | 1.94 | 78.2 |
|  |  |  |  |  |  | 11 | 92.7 | 98.8 | 69.83 | 1.99 | 79.1 |
|  |  |  |  |  |  | 12 | 91.3 | 99.0 | 67.41 | 1.73 | 77.2 |
|  |  |  |  |  |  | 13 | 91.8 | 99.1 | 68.38 | 1.80 | 77.9 |
|  |  |  |  |  |  | 14 | 92.0 | 99.1 | 69.03 | 1.70 | 78.1 |
|  |  |  |  |  |  | 15 | 91.8 | 99.4 | 69.39 | 1.68 | 78.6 |
|  |  |  |  |  |  | 16 | 92.0 | 99.2 | 69.11 | 1.67 | 78.3 |
|  |  |  |  |  |  | 17 | 91.9 | 99.3 | 69.54 | 1.60 | 78.5 |
|  |  |  |  |  |  | 18 | 92.1 | 99.3 | 69.79 | 1.66 | 78.7 |
|  |  |  |  |  |  | 19 | 92.0 | 99.3 | 69.99 | 1.63 | 78.9 |

TABLE 2-continued

Gas Phase Isomerization of 2M3BN to 3PN and 4PN at 145° C.

| Ex. | Catalyst (Support) | Catalyst g, wt. % Ni | 2M3BN Feed mmole/hr | N2 Feed mL/min | 2M3BN/Ni mole/gramatom | Elapsed Time Hr. | % Conv. | % PN/ Total | (3PN) GC Area % | (4PN) | % Useful PN |
|---|---|---|---|---|---|---|---|---|---|---|---|
| | | | | | | 20 | 91.6 | 99.3 | 69.33 | 1.50 | 78.3 |
| | | | | | | 21 | 92.0 | 99.3 | 69.40 | 1.60 | 78.2 |
| | | | | | | Feed | 10.9 | 78.5 | 0.12 | — | 81.5 |

TABLE 3

Gas Phase Isomerization of 2M3BN to 3PN and 4PN at 145° C.

| Ex. | Catalyst (Support) | Catalyst g, % Ni | 2M3BN Feed mmole/hr | N2 Feed mL/min | 2M3BN/Ni mole/ gramatom | Elapsed Time Hr. | % Conv. | % PN/ Total | (3PN) GC Area % | (4PN) | % Useful PN |
|---|---|---|---|---|---|---|---|---|---|---|---|
| 13 | Ni[OTTP]2CH2=CH2 ÷ "A" (SiO2) | 1.01, 0.31 | 2.06 | 10 | 23.6 | 0.75 | 92.7 | 89.3 | 58.92 | 4.89 | 77.7 |
| | | | | | | 1.75 | 93.0 | 98.4 | 67.89 | 4.63 | 79.5 |
| | | | | | | 2.75 | 92.0 | 98.9 | 69.00 | 4.13 | 79.9 |
| | | | | | | 3.75 | 91.5 | 98.2 | 67.24 | 3.38 | 78.3 |
| | | | | | | 4.75 | 92.3 | 99.1 | 69.96 | 3.38 | 80.1 |
| | | | | | | 5.75 | 92.5 | 99.3 | 68.65 | 3.72 | 79.0 |
| | | | | | | 6.75 | 93.1 | 99.2 | 70.37 | 3.46 | 80.0 |
| | | | | | | 7.75 | 93.1 | 98.9 | 70.58 | 3.28 | 80.1 |
| | | | | | | 8.75 | 90.4 | 99.2 | 60.66 | 2.91 | 72.7 |
| | | | | | | 9.75 | 93.3 | 99.4 | 70.96 | 3.34 | 80.3 |
| | | | | | | 10.75 | 90.2 | 99.3 | 66.34 | 2.68 | 76.4 |
| | | | | | | 11.75 | 91.7 | 99.2 | 62.88 | 2.81 | 73.5 |
| | | | | | | 11.75 | 91.1 | 99.3 | 68.14 | 2.68 | 78.9 |
| | | | | | | 13.75 | 93.7 | 98.8 | 73.29 | 2.82 | 80.5 |
| | | | | | | 14.75 | 93.0 | 98.9 | 65.63 | 2.59 | 75.8 |
| | | | | | | 16.75 | 90.8 | 99.6 | 66.18 | 2.53 | 76.7 |
| | | | | | | 17.75 | 92.8 | 97.9 | 68.85 | 2.86 | 79.2 |
| | | | | | | 18.75 | 93.0 | 98.3 | 70.76 | 2.89 | 78.8 |
| | | | | | | 19.75 | 93.2 | 99.0 | 71.84 | 2.61 | 79.6 |
| | | | | | | 20.75 | 92.6 | 98.5 | 70.76 | 2.45 | 80.4 |
| | | | | | | Feed | 10.9 | 99.5 | 1.37 | — | 87.9 |

Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than to the foregoing specification, as indicating the scope of the invention.

What is claimed is:

1. A process for the gas phase isomerization of an acylic, aliphatic, nonconjugated 2-alkyl-3-monoalkenenitrile comprising, contacting the starting nitrile, at a temperature within the range of 135° C. to 170° C. with a supported catalyst composition comprising zerovalent nickel and at least one bidentate phosphite ligand selected from the group consisting of Formula I and II:

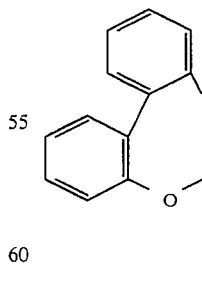
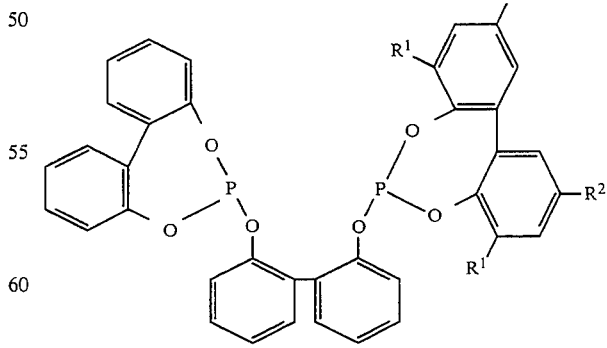

Formula I wherein
each $R^1$, independently, is a secondary or tertiary hydrocarbyl of 3 to 12 carbon atoms;
each $R^2$, independently, is H, a $C_1$ to $C_{12}$ alkyl, or $OR^3$, wherein $R^3$ is $C_1$ to $C_{12}$ alkyl; and

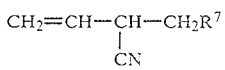

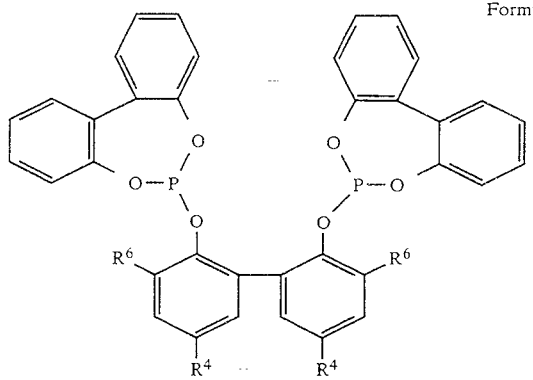

wherein each $R^4$, independently, is a tertiary hydrocarbon of up to 12 carbon atoms, or $OR^5$, wherein $R^5$ is a $C_1$ to $C_{12}$ alkyl; and each $R^6$, independently, is a tertiary hydrocarbon of up to 12 carbon atoms, to produce nonconjugated, linear, acyclic 3- and/or 4-monoalkenenitriles.

2. The process of claim 1 wherein the reaction temperature is 140°–160° C.

3. The process of claim 2 wherein the reaction temperature is 145°–150° C.

4. The process of claim 1 wherein the starting 2-alkyl-3-monoalkenenitrile is a compound represented by the following Formula $$CH_2=CH-\underset{CN}{CH}-CH_2R^7$$

wherein $R^7$ is H or a $C_1$ to $C_3$ alkyl.

5. The process of claim 4 wherein the starting nitrile is 2-methyl-3-butenenitrile.

6. The process of claim 1 wherein the starting 2-alkyl-3-monoalkenenitrile is further substituted with at least one other group which does not adversely affect the catalyst.

7. The process of claim 1 wherein the isomerization is carried out at a pressure of 101.3 kPa to 1013 kPa.

8. The process of claim 1, wherein the isomerization is carried out in a continuous manner, at a feed rate such that the mole ratio of starting 2-alkyl-3-alkenenitrile to catalyst is between 5:1/hour. to 100:1/hour.

9. The process of claim 1 wherein the catalyst is supported on a carrier selected from the group consisting of silica, alumina, and carbon.

10. The process of claim 1 wherein the starting 2-alkyl-3-alkenenitrile is introduced into the isomerization reaction as neat vapor.

11. The process of claim 1 wherein the starting 2-alkyl-3-alkenenitrile is introduced into the isomerization reaction as a vaporized solution in a volatile solvent.

12. The process of claim 11 wherein the solvent is selected from the group consisting of saturated and aromatic hydrocarbons and aliphatic nitriles which are gaseous at the isomerization reaction temperature.

* * * * *